United States Patent [19]
Kuo et al.

[11] Patent Number: 5,973,165
[45] Date of Patent: Oct. 26, 1999

[54] PROCESS FOR PREPARING 2-OXINDOLE

[75] Inventors: Lung-Huang Kuo; Jaan-Pyng Hsu; Chin-Tsai Chen, all of Kaohsiung, Taiwan

[73] Assignee: Sinon Corporation, Taiwan

[21] Appl. No.: 09/270,945

[22] Filed: Mar. 17, 1999

[51] Int. Cl.[6] .................................................. C07D 209/34

[52] U.S. Cl. ............................................................ 548/486

[58] Field of Search ............................................... 548/486

[56] References Cited

PUBLICATIONS

Crestini et al., A New Efficient and Mild Synthesis of 2–Oxindoles . . . , Synth. Comm., 24(40), 2835–2841, Dec. 1994.

*Primary Examiner*—Johann Richter
*Assistant Examiner*—Dominic Keating
*Attorney, Agent, or Firm*—Fish & Richardson P.C.

[57] ABSTRACT

A process for preparing 2-oxindole includes catalytically reacting isatin with hydrazine hydrate in a polar solvent containing a dissolved weak base at an elevated temperature to form the 2-oxindole product.

14 Claims, No Drawings

PROCESS FOR PREPARING 2-OXINDOLE

BACKGROUND OF THE INVENTION

1. Field of the invention

This invention relates to a process for preparing 2-oxindole compound, more particularly to a process which involves catalytically reacting isatin with hydrazine hydrate in a polar solvent in the presence of a weak base to form the 2-oxindole compound.

2. Description of the related art

Oxindoles, which have the following structure (structure I):

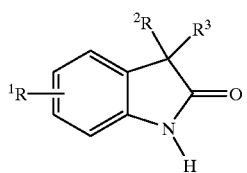

are known as an intermediate in making certain types of pharmaceutical related products, such as adibendan (structure II), a cardiotonic agent for congestive

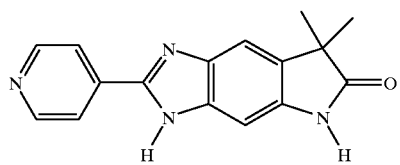

heart failure, which comprises an oxindole moiety (structure I). Various tyrosine kinase inhibitors, which are useful for regulating epidermal growth, are also prepared from 2-oxindole. The 2-oxindole (structure III) can be substituted or unsubstituted, and has the following structure:

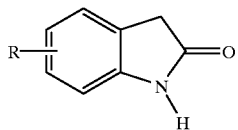

wherein R is an alkyl, alkoxyl, aryl, phenoxy, halogen, or hydrogen.

It has been known in the art that 2-oxindole can be prepared by a method (D. S. Soriano, J. Chem. Edu., 1993, 70, 332) illustrated by the following reaction:

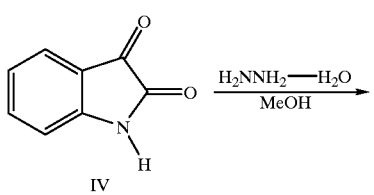

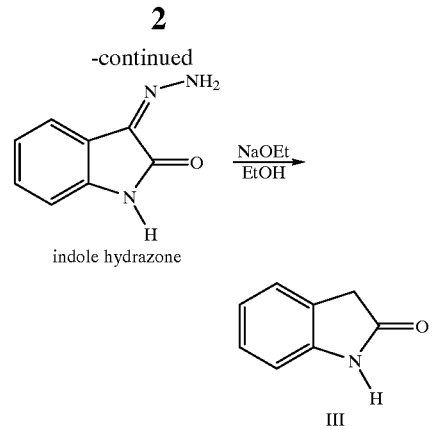

In this method, isatin (structure IV) is reacted with hydrazine hydrate in an anhydrous methanol to form an intermediate (i.e. indole hydrazone) in a suspended form in the reaction mixture. The intermediate is then separated from the reaction mixture and purified by crystallizing means. The purified intermediate is dried and subjected to the Wolf-Kishner reduction in an anhydrous ethanol solution in the presence of a strong base, such as sodium ethoxide, at an elevated temperature so as to yield the 2-oxindole product. The yield of the 2-oxindole obtained by this method can reach up to 69%.

The method described above is complicated because of its requirement for separating, purifying, and drying steps in the process of preparing the 2-oxindole. The method also requires the use of expansive anhydrous ethanol as solvent in the reaction mixture because sodium ethoxide can react with water and therefore lose its activity for catalyzing the reaction. In addition, this method uses a large amount of sodium ethoxide which is normally prepared by reacting sodium with anhydrous ethanol. Since sodium is extremely active and dangerous, the use of sodium ethoxide would give rise to safety concerns for this method.

Another method of preparing 2-oxindole is described by Crestini and Saladino, Synth. Commun. 1994, 24, 2835, and is illustrated by the following reaction:

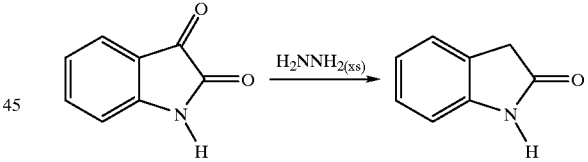

In this method, isatin is first dissolved in pure hydrazine, and then reacted with pure hydrazine under heat to form the 2-oxindole product. The yield of the 2-oxindole obtained by this method can reach up to 76%.

The method described above requires the use of a large amount of pure hydrazine to dissolve the isatin for later reaction. It is known that pure hydrazine can cause severe explosion hazard when exposed to heat or reaction with oxidizers. Hence, the use of pure hydrazine requires extreme caution, which makes this method impractical.

Both methods described above are reported to use a high temperature of about 200° C. for the reaction to take place. Such high temperature would consume much energy, and in the case that a strong base is used as a catalyst, results in the need of a reactor made from a special material for anti-corrosion purpose.

SUMMARY OF THE INVENTION

Therefore, it is an object of the present invention to provide a process for preparing 2-oxindole that dispenses with the need to use a strong base or pure hydrazine in the process, thereby overcoming the disadvantages described above.

According to the present invention, a process for preparing 2-oxindole compound comprises catalytically reacting isatin with hydrazine hydrate in a polar solvent in the presence of a weak base to form a crude 2-oxindole product.

DETAILED DESCRIPTION OF THE PREFERRED EMBODIMENTS

This invention will now be described in greater detail in the following detailed description including the Examples and Comparative Examples provided herein.

According to the present invention, it has been surprisingly found that, instead of using a strong base as a catalyst in the aforementioned method, the weak base used in the process of this invention gave unusually good results, i.e. the reaction of isatin with hydrazine hydrate catalyzed by carefully selecting the weak base and the polar solvent in the reaction mixture according to the process of this invention gave a higher yield than those obtained from the aforementioned methods.

The polar solvent used in the method of this invention is preferably selected from the group consisting of water, ethanol, 1-propanol, 2-propanol, 2-methyl-1-propanol, 2-methyl-2-propanol, 1-butanol, 2-butanol, 1-methyl-2-pyrrolidinone, N,N'-dimethylformamide, N,N'-dimethylacetamide, dimethylsulfoxide, and mixtures thereof. The more prefered polar solvent is N,N'-dimethylformamide.

The weak base acts as catalyst for the reaction of isatin with hydrazine hydrate, and is preferably selected from the group consisting of alkali carbonates, alkali acetates, and mixtures thereof. The more prefered weak base is sodium acetate.

The crude 2-oxindole product obtained from the process of the present invention can be purified by the following steps: (a) dissolving the crude 2-oxindole in a solvent to form a solution; (b) adding activated carbon to said solution for decolorizing said solution; and (c) removing activated carbon from the solution and crystallizing said solution to form a precipitate of 2-oxindole.

The solvent used in the purification of the crude 2-oxindole product described above is preferably selected from the group consisting of dichloromethane, hexane, 1,2-dichloroethane, toluene, ethyl acetate, 2-propanol, isopropyl ether, ethanol, 1,2-dichloroethane, water, and mixtures thereof. The more preferred solvent is 1,2-dichloroethane. The activated carbon is preferably added in an amount of 3 to 10% by weight based on the weight of the crude 2-oxindole product. The more preferred amount is 5% by weight.

In practice, the preparation of the 2-oxindole according to the process of the present invention is preferably carried out at a reaction temperature in the range from 60 to 250° C., particularly at 100° C., and at a mole ratio of a weak base of sodium acetate to isatin in a range of from 0.03:1 to 0.3:1. Also, the molar concentration of isatin present in the polar solvent during the reaction is preferably from 0.2 to 3.5 M.

The following Examples and Comparative Examples illustrate the unexpectedly better results of this invention over the aforesaid prior art.

EXAMPLE 1

166 g (1.1 mole) of isatin was dissolved in 650 ml of N,N'-dimethylformamide in a flask. 70 ml of 80% hydrazine hydrate (1.1 mole) uniformly mixed with 180 ml of N,N'-dimethylformamide was added in drops into the flask. Afterwards, 8.3 g of sodium acetate (0.1 mole) was added into the flask, and the temperature of the reaction mixture was raised to 100° C. for the reaction of isatin with hydrazine hydrate for 8 hrs. After the reaction was completed, the polar solvent was distilled off from the reaction mixture, and the remaining mixture was added with 500 ml of water. The resulting mixture was then extracted by 500 ml of toluene twice. The extract was dried to give about 142 g of yellowish colored solid of crude 2-oxindole. The gross yield and the purity of the 2-oxindole so-obtained were about 95% and 97%, respectively. The crude 2-oxindole was dissolved in 420 ml of dichloroethane under heat, and was decolorized by adding 7.1 g (about 5% by weight based on the weight of the crude 2-oxindole) of activated carbon. The activated carbon was removed by filtering means to give a colorless solution. This solution was then cooled to allow the 2-oxindole to be precipitated out by crystallization. The crystallized 2-oxindole was separated from the solution, and was dried to give 128 g of white powered solid of 2-oxindole. The total yield and the purity of the 2-oxindole were 85% and 99.5%, respectively.

EXAMPLES 2–4

Example 1 was repeated, except that the polar solvent was 1-methyl-2-pyrolidinone, N,N-dimethylacetamide, and dimethylsulfoxide, respectively, for Examples 2–4. The yield of Examples 2 to 4 are 59%, 72%, and 61%, respectively.

EXAMPLE 5

Example 1 was repeated, except that the weak base was sodium carbonate and the mole ratio of isatin: hydrazine hydrate:sodium carbonate was 1:1:0.04. The yield of this Example was 61%.

EXAMPLE 6

Example 1 was repeated, except that the weak base was potassium carbonate and the mole ratio of isatin hydrazine hydrate:potassium carbonate was 1:10.03. The yield of this Example was 52%.

EXAMPLE 7

Example 1 was repeated, except that the molar concentration of isatin in the N,N'-dimethylformamide was 3.4 M, the weak base was sodium carbonate and the mole ratio of isatin:hydrazine hydrate:sodium carbonate was 1:1:0.09. The yield of this Example was 68%.

EXAMPLE 8

Example 1 was repeated, except that the molar concentration of isatin in the N,N'-dimethylformamide was 3.4 M, the weak base was potassium carbonate, and the mole ratio of isatin:hydrazine hydrate:potassium carbonate, was 1:1:0.07. The yield of this Example was 65%.

COMPARATIVE EXAMPLE 1

Example 1 was repeated, except that the weak base was replaced with a strong base, i.e. lithium hydroxide, and the mole ratio of isatin:hydrazine hydrate:lithium hydroxide was 1:1:0.2. The yield of this Example was 64%.

COMPARATIVE EXAMPLE 2

Example 1 was repeated, except that the weak base was replaced with a strong base, i.e. sodium hydroxide, and the mole ratio of isatin:hydrazine hydrate:sodium hydroxide was 1:1:0.1. The yield of this Example was 66%.

COMPARATIVE EXAMPLE 3

Example 1 was repeated, except that the weak base was replaced with ca strong base, i.e. potassium hydroxide, and the mole ratio of isatin:hydrazine hydrate potassium hydroxide was 1:1:0.08. The yield of this Example was 63%.

COMPARATIVE EXAMPLE 4

Example 1 was repeated, except that the molar concentration of the isatin was 3.4 M, the weak base was replaced with a strong base, i.e. lithium hydroxide, and the mole ratio of isatin:hydrazine hydrate:lithium hydroxide was 1:1:0.4. The yield of this Example was 52%.

COMPARATIVE EXAMPLE 5

Example 1 was repeated, except that the molar concentration of the isatin was 3.4 M, the weak base was replaced with strong base, sodium hydroxide, and the mole ratio of isatin:hydrazine hydrate:sodium hydroxide was 1:1:0.2. The yield of this Example was 57%.

COMPARATIVE EXAMPLE 6

Example 1 was repeated, except that the molar concentration of the isatin was 3.4 M, the weak base was replaced with a strong base, i.e. potassium hydroxide, and the mole ratio of isatin:hydrazine hydrate:potassium hydroxide was 1:1:0.1. The yield of this Example was 54%.

COMPARATIVE EXAMPLE 7

Example 1 was repeated, except that the polar solvent was ethylene glycol, the molar concentration of the isatin was 0.2 M, the weak base was replaced with a strong base, i.e. potassium hydroxide, and the mole ratio of isatin:hydrazine hydrate:potassium hydroxide was 1:1:1. The reaction temperature was kept at 140° C. The yield of this Example was 51%.

COMPARATIVE EXAMPLE 8

Example 1 was repeated, except that the polar solvent was ethanol, the molar concentration of the isatin was 0.2 M, the weak base was replaced with a strong base, i.e. sodium methoxide, and the mole ratio of isatin:hydrazine hydrate::sodium methoxide was 1:3:1. The react-ion temperature was kept at 80° C. The yield of this Example was 27%.

It is clearly seen from the results of the Examples and the Comparative Examples that the yield of 2-oxindole can be improved by carefully selecting the weak base and the polar solvent for the reaction of isatin with hydrazine hydrate according to the process of the present invention.

With the invention thus explained, it is apparent that various modifications and variations can be made without departing from the spirit of the present invention. It is therefore intended that the invention be limited only as recited in the appended claims.

We claim:

1. A process for preparing 2-oxindole compound having the following general structure:

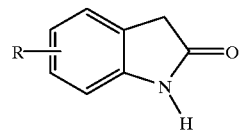

wherein R is an alkyl, alkoxy, aryl, phenoxy, halogen, or hydrogen, said process comprising:

catalytically reacting isatin with hydrazine hydrate in a polar solvent in the presence of a weak base to form a crude 2-oxindole.

2. The process of claim 1, wherein said polar solvent is selected from the group consisting of water, ethanol, 1-propanol, 2-propanol, 2-methyl-1-propanol, 2-methyl-2-propanol, 1-butanol, 2-butanol, 1-methyl-2-pyrrolidinone, N,N'-dimethylformamide, N,N'-dimethylacetamide, dimethylsulfoxide, and mixtures thereof.

3. The process of claim 2, wherein said polar solvent is N,N'-dimethylformamide.

4. The process of claim 1, wherein said weak base is selected from the group consisting of alkali carbonates, alkali acetates, and mixtures thereof.

5. The process of claim 4, wherein said weak base is sodium acetate.

6. The process of claim 5, wherein the mole ratio of said sodium acetate to said isatin is in a range of from 0.03:1 to 0.3:1.

7. The process of claim 1, wherein the reaction takes place at a temperature from 60 to 250° C.

8. The process of claim 7, wherein the temperature is 100° C.

9. The process of claim 1, wherein the molar concentration of said isatin present in said polar solvent ranges from 0.2 to 3.5 M.

10. The process of claim 1, further comprising the following steps:

(a) dissolving the crude 2-oxindole in a solvent to form a solution;

(b) adding activated carbon to said solution for decolorizing said solution; and (c) removing activated carbon from the solution and crystallizing said solution to form a precipitate of 2-oxindole.

11. The process of claim 10, wherein said solvent is selected from the group consisting of dichloromethane, hexane, 1,2-dichloroethane, toluene, ethyl acetate, 2-propanol, isopropyl ether, ethanol, 1,2-dichloroethane, water, and mixtures thereof.

12. The process of claim 11, wherein said solvent is 1,2-dichloroethane.

13. The process of claim 10, wherein said activated carbon is added in an amount of 3 to 10% by weight based on the weight of said crude 2-oxindole.

14. The process of claim 13, wherein said activated carbon is added in an amount of 5% by weight based on the weight of said crude 2-oxindole.

* * * * *